United States Patent [19]

Miyajima et al.

[11] Patent Number: 4,926,862
[45] Date of Patent: May 22, 1990

[54] DEFIBRILLATION SYSTEM

[75] Inventors: Nobukazu Miyajima, Tokorozawa; Akira Tanaka, Okegawa; Masaru Shinoda, Tokyo, all of Japan

[73] Assignee: Nihon Kohden Corporation, Tokyo, Japan

[21] Appl. No.: 216,823

[22] Filed: Jul. 8, 1988

[30] Foreign Application Priority Data

Jul. 11, 1987 [JP] Japan .................. 62-106745[U]

[51] Int. Cl.⁵ .............................................. A61N 1/00
[52] U.S. Cl. ......................... 428/419 D; 128/419 PS; 128/419 S
[58] Field of Search ........... 128/419 D, 419 S, 419 R, 128/419 PT, 419 PS

[56] References Cited

U.S. PATENT DOCUMENTS

| Re. 30,387 | 8/1980 | Denniston, III et al. | 128/419 D |
| 4,233,659 | 11/1980 | Pirkle | 128/419 D |
| 4,574,810 | 3/1986 | Lerman | 128/419 D |
| 4,823,796 | 4/1989 | Benson | 128/419 D |

Primary Examiner—Francis Jaworski
Assistant Examiner—George Manuel
Attorney, Agent, or Firm—Hoffmann & Baron

[57] ABSTRACT

A defibrillation system including a high voltage metallized plastic film capacitor which is charged to a high voltage and is discharged to the body of the patient by way of a paddle. The defibrillation system includes a charge abnormality detection circuit for detecting dielectronic breakdown of the capacitor, a notifier for notifying the operator of the system of detection of charge abnormality in response to the detection signal produced by the detection circuit, and a switch circuit for inhibiting the feeding of high voltage to the capacitor in a high voltage generating cirucit, in response to a detection signal. Other aspects of the present invention include a metallized plastic film capacitor construction including a plurality of capacitor elements each of which is formed from wound-up metallized plastic films and to which metallic contacts and capacitor terminals are provided along with external resistances, as to reduce the production of loud noise during dielectric breakdown, in particular.

6 Claims, 3 Drawing Sheets

DEFIBRILLATION SYSTEM

BACKGROUND OF THE INVENTION

1. Field of the Invention

The present invention relates to apparatus for providing high voltage discharge to a patient, and more particularly to a defibrillation system in which a high voltage generating circuit charges a high voltage capacitor circuit using high voltage, and which is adapted to apply the high voltage charge to a patient's body by way of a paddle, upon closing an output switch.

2. Setting for the Invention

Conventional defibrillation systems often employ a high voltage capacitor circuit using a capacitor having metalfilm type electrodes and terminals having a tab structure with which lead wires can be inserted. Such capacitors tend to be bulky for use in high voltage capacitor circuits and present serious problems since the durable life of such capacitors are quite limited due to the fact that the lead wires thereof tend to fail when subjected to high stress typically accompanying normal operation, and due to the fact that the lead wires tend to deteriorate during the discharge of electrical current of large magnitude.

One prior art solution to the above-described problem has been to use metallized plastic film capacitors in the high voltage capacitor circuits of prior art defibrillation systems. In such systems, however, another significant problem arises regarding the performance of the metallized plastic film capacitors when being charged with high voltage. In particular, when metallized plastic film capacitors are subjected to high voltages such that they undergo dielectric breakdown, such capacitors are capable of preventing self-destruction during breakdown which is referred to as a "self-healing" action, and consequently are charged again with a high voltage which is lower than the prescribed voltage applied to the capacitor. In many cases, a metallized plastic film capacitor undergoing dielectric breakdown is unstable and is not in a condition suitable for active defibrillation.

In a metallized plastic film capacitor, the electrodes are composed of the positive layers and the lead wires extend from the metallic contact (i.e. metal sprayed) portions at both ends of the wound-up films. Although this arrangement makes it possible to reduce the parameter "tangent δ", it raises another problem. In particular, when dielectric breakdown occurs, short circuiting current may flow locally in the capacitor producing a loud noise similar to an explosion. Thus while metallized plastic film capacitors for use in high voltage capacitor circuits have advantages, the self-healing action and loud noise production during dielectric breakdown has made their use much less than desirable.

In view of the above-described shortcomings and drawbacks of metallized plastic film capacitors used in defibrillation systems, there is a great need for an effective solution to such accompanying problems.

Accordingly, it is the primary object of the present invention to solve such problems by providing a defibrillation system which includes a high voltage capacitor circuit using a metallized plastic film capacitor, and which is capable of automatically detecting the occurrance of dielectric breakdown of the high voltage capacitor and thereupon automatically ceasing the operation of the system.

Another object of the present invention is to provide a high voltage capacitor utilizing metallized plastic film capacitor elements, which is suitable for use in a defibrillation system.

According to the present invention, the defibrillation system comprises a high voltage generating circuit, a high voltage capacitor circuit, an output circuit, a charge abnormality detection circuit, a notifying means, and a switch circuit.

The high voltage capacitor circuit is adapted to be charged with the high voltage produced by the high voltage generating circuit, and includes a metallized plastic film capacitor. The output circuit includes a switch and is adapted to apply the high voltage to a paddle mounted on the body of a patient. The charge abnormality detection circuit detects either a sharp increase in charge current or a sharp drop in charge voltage which is caused by dielectric breakdown of the metallized plastic film capacitor. The notifying means responds to a detection signal produced by the charged abnormality detection circuit, and the switch circuit in response to the detection signal inhibits the feeding of the high voltage from the high voltage generating circuit to the high voltage capacitor circuit.

This arrangement makes possible the detection and notification of sharp drops in charge voltage and sharp increases in electrical currents associated with dielectric breakdown of the high voltage capacitor. Thus, even if a metallized plastic film capacitor is used as a high voltage capacitor of the defibrillation system, the present invention eliminates the problem arising as a result of the self-healing characteristics of the metallized plastic film capacitor, i.e. recharging thereof with an insufficiently high voltage and subsequent operation in and under unstable conditions.

Further, the metallized -plastic film capacitor of the present invention comprises a plurality of capacitor elements each of which have wound-up metallized plastic films and metallic contacts provided on the end surfaces of both sides thereof. Resistors each having a resistance at least equal to the internal resistance of each capacitor element per se, are connected to the metallic contact portions of the capacitor elements. By virtue of this arrangement, the high voltage capacitor for the defibrillation system hereof is made compact. In addition, since the capacitor is divided into a plurality of elements, the number of times the thin metal layers must be wound is reduced, thereby facilitating manufacture while improving the performance reliability of the capacitor.

Moreover, in the event of dielectric breakdown, short-circuiting discharge of capacitor elements are allowed to take place via the additional resistors, thereby avoiding any localized discharge and thereby reducing the level of noise associated with dielectric breakdown.

BRIEF DESCRIPTION OF THE DRAWINGS

For further understanding of the objects of the present invention, reference is made to the following detailed description of the preferred embodiment which is to be taken in connection with the accompanying drawings, wherein.

DETAILED DESCRIPTION OF THE PREFERRED EMBODIMENT

Figure 1:
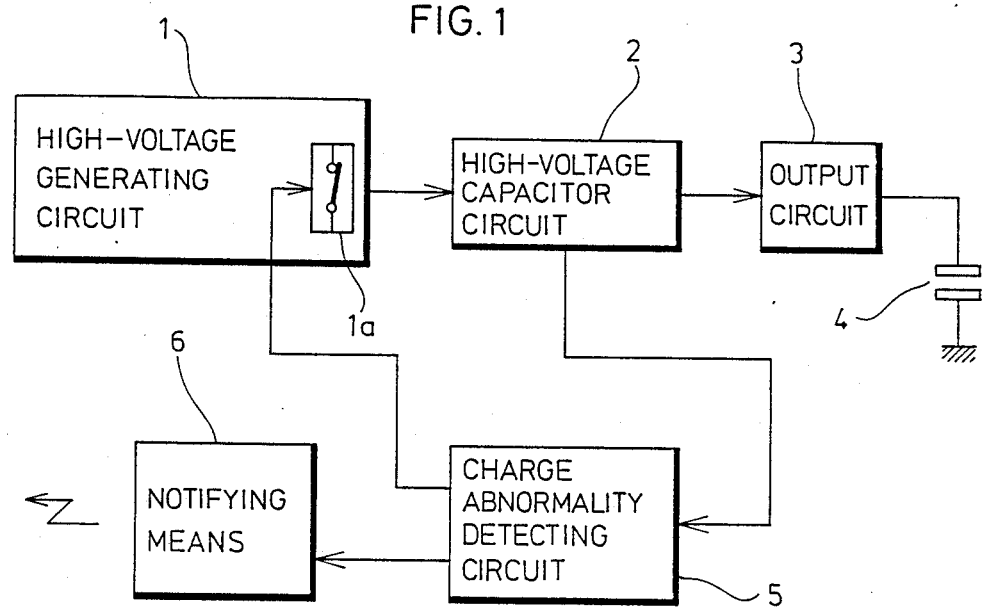
FIG. 1 is a diagram showing the basic circuit arrangement of a defibrillation system constructed in accordance with the present invention.

Referring to FIG. 1, defibrillation systems commonly known in the art include in principle, a high-voltage generating circuit 1, a high-voltage capacitor circuit 2 adapted to be charged with a high-voltage by the circuit 1, and an output circuit 3 including at least a switch for applying high-voltage to a paddle 4 mounted to the body of a patient who is to undergo a defibrillation or other cardiac procedure. For each of these components, there are various non-structures available.

According to the present invention, the defibrillation system further comprises a charge abnormality detection circuit 5, a notifying means 6, a switch circuit 1a, and the high-voltage capacitor circuit 2, which includes a metallized plastic film capacitor. The charge abnormality detection circuit 5 detects either a sharp increase in charge current or a sharp drop in charge voltage which is caused by a dielectric breakdown of the metallized plastic film capacitor, whereas the notifying means 6 serves to notify an abnormality in charged voltage or current, in response to the production of a detection signal by the charge abnormality detecting circuit 5. Notification is given to the operator by the notifying means 6 emitting light or sound. The switch circuit 1a, on the other hand, serves to inhibit the feeding of high-voltage to the high-voltage capacitor circuit 2, or in response to the detection signal, by blocking the voltage input to the high voltage generating circuit 1 or by ceasing the operation of the high voltage generating circuit 1 altogether.

Once a dielectric breakdown occurs in the metallized plastic film capacitor serving in the high voltage capacitor circuit 2, the charge abnormality detection circuit 5 detects abnormality in the charging of the capacitor, or in the charge condition of the capacitor during the charging process or after the completion of charging of the capacitor. Upon the detection of charge abnormality, the switch circuit 1a inhibits the feeding of high voltage to the metallized plastic film capacitor, thereby preventing the capacitor from being recharged by the self-healing action of such types of capacitors. Simultaneously, the notifying means 6 notifies the operator that dielectric breakdown of the capacitor has occurred, thus enabling the capacitor to be replaced and thereby eliminating the risk of a "self-healed" capacitor being used in a condition having a low charge capacity.

Figure 2:
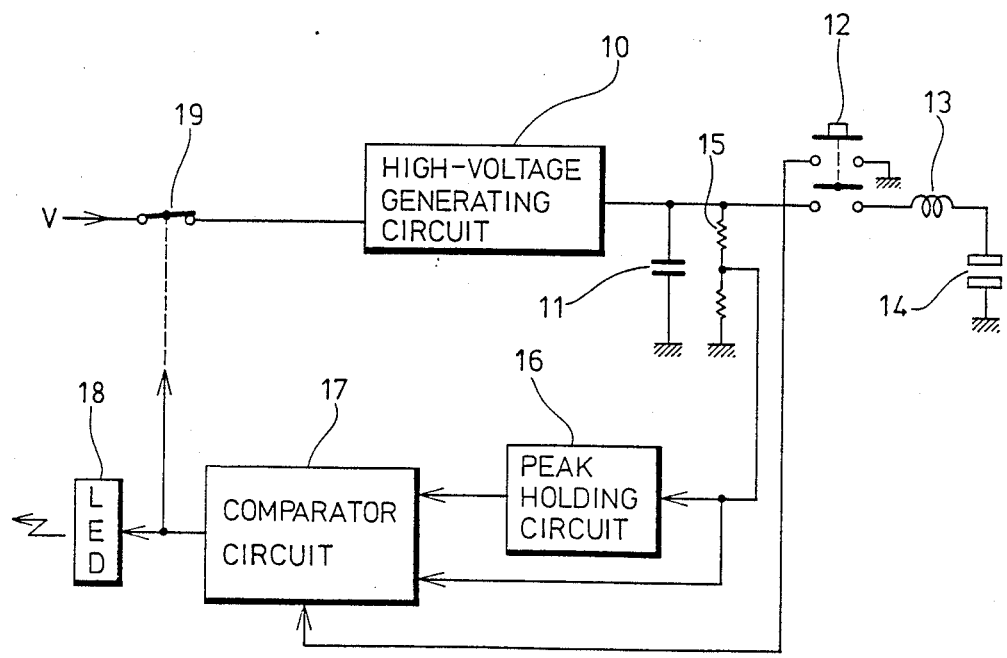
FIG. 2 is a diagram showing a circuit arrangement of the defibrillation system constructed in accordance with one embodiment of the present invention.

FIG. 2 shows the circuit arrangement of a defibrillation system constructed in accordance with a specific embodiment of the present invention.

Referring to FIG. 2 the arrangement of the defibrillation system is such that a high voltage capacitor 11 is charged by a high-voltage generating circuit 10, and, when switch 12 is energized, the charge voltage of a high voltage capacitor 11 is applied to paddle 14 via an inductance 13. According to the present invention, the defibrillation system is provided with a charge abnormality detection circuit. This circuit comprises a voltage divider 15 for the high voltage capacitor 11, a peak holding circuit 16 to which a fraction voltage of the voltage divider 15 is input, and a comparator circuit 17. The holding voltage of the circuit 16 is provided as input to the comparator circuit 17 which is adapted to generate a signal when the fraction voltage drops below ¾ of the holding voltage. The output of the comparitor circuit 17 is applied to an LED 18 for notifying abnormality, and simultaneously is used to drive a switch 19 for blocking the voltage input to the high voltage generating circuit 10.

Figure 3:
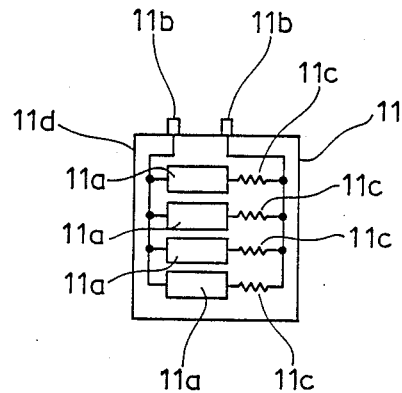
FIG. 3 is a schematic illustration showing the arrangement of a high-voltage capacitor of the defibrillation system for the present invention.

As shown in FIG. 3, the high-voltage capacitor 11 includes a plurality of capacitor elements 11a which are received in a common case 11d. Each of the capacitor elements 11a is formed from wound-up metallized plastic films and is provided with metallic contacts at the ends of both sides thereof. The metallic contact portions (at the ends on either side of the capacitor elements) are connected to either one of a pair of capacitor terminals 11b extending from the case 11d. The arrangement of this connection is such that the plurality of resistors 11c which each have the same resistance as the internal resistance of each capacitor element 11a per se, are interposed between the metallic contact portions provided on the ends at least on one side of the elements 11a and the corresponding terminal.

The comparator circuit 17 is maintained inoperative during a discharging period so as to prevent the circuit 17 from being erroneously actuated by a drop in voltage during the discharge of the high voltage capacitor 11 via the paddle 14 to the living organism after switch 12 has been energized (i.e. closed).

The operation of the defibrillation system is as follows.

While the capacitor is being charged, the voltage across the capacitor 11 rises according to a saw-tooth waveform so that the holding voltage of the peak holding circuit is sequentially renewed and the circuit 16 holds the voltage corresponding to the charged voltage. Thus during a charging period, signals input to the terminals of the comparator circuit 17 are at substantially the same level and the circuit 17 generates no signal. When the switch 12 is closed after the completion of charging, the electrical charge in the high voltage capacitor 11 is discharged to the body via the paddle 14. During this discharging period, a control signal is supplied from the switch 12 to the comparator circuit 17 so that the circuit 17 will not detect any difference between the holding voltage and the voltage sensed at the voltage divider 15.

However, if a dielectric breakdown occurs either during the charging of the capacitor 11, before the closing of switch 12, or after the completion of the capacitor charging process, then the dielectric breakdown causes a sharp drop in the charge voltage across capacitor 11 so as to reduce the fraction voltage at 15 below the threshold, i.e three-fourths of the peakholding voltage. Upon detection of dielectric breakdown, the comparator circuit outputs the detection signal. In the response to the detection signal, LED 18 is energized in order to notify the operator of the occurrence of dielectric breakdown of the capacitor 11, and simultaneously switch 19 is operated to interrupt the generation of high voltage. In this arrangement, the capacitor 11 is positively prevented from being recharged by the self-healing characteristics of the metallized plastic film capacitor. By virtue of the interposition of the resistors 11c, the flow of short-circuiting current from one element 11a to others, as a result of dielectric breakdown, can thus be controlled by the corresponding time constant formed by the resistors and capacitors, thereby reducing the level of noise occurring during dielectric breakdown.

In the foregoing embodiment, the charge abnormality detection circuit may alternatively be such that, instead of the capacitor 11 being connected to the voltage divider 15, capacitor 11 is serially connected to resistors of a small resistance which are provided for the purpose of detecting the charge current, and a differentiation circuit is provided in order to detect a sharp increase in current, which occurs as a result of dielectric breakdown.

Figure 4:
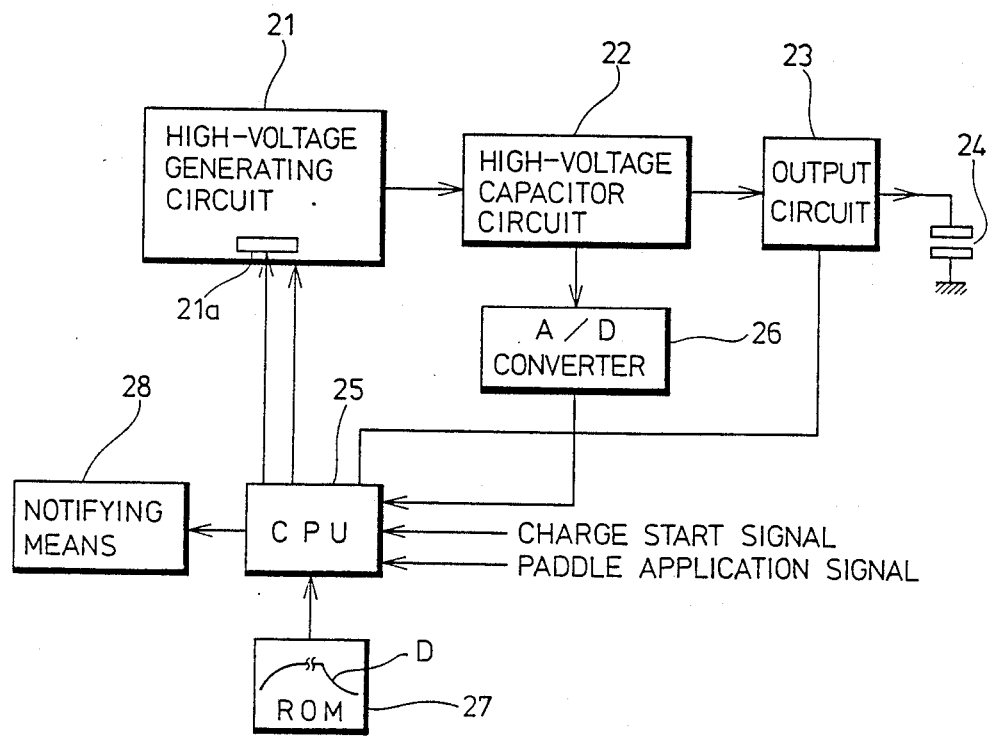
FIG. 4 is a diagram showing a circuit arrangement of a defibrillation system constructed in accordance with an alternative embodiment of the present invention.

FIG. 4 illustrates the embodiment of the present invention. The defibrillation system of FIG. 4 comprises a high voltage generating circuit 21, a high voltage capacitor circuit 22, an output circuit 23, a paddle 24, and a central processing unit (CPU) 25 provided for the purpose of control. According to this embodiment, the CPU 25 is used in the following manner. A fraction of the high voltage which has been digitized by an A/D convertor 26 is fed to the CPU 25 to be compared, as time passes, with normal charging and discharging characteristics (i.e. data D) which are stored in a Read-Only-Memory (ROM) 27. Notably, the normal charging and discharging characteristics (data D) stored in ROM 27 represent the voltages across the high voltage capacitor during normal charging and discharging of the capacitor to a patient. Using this embodiment of the invention, there is continuous monitoring of the charged voltage across the high voltage capacitor in the high voltage capacitor circuit 22.

If a change in the charge voltage causes the charge voltage to deviate from the discharging curve data D by a large predetermined value, then detection of dielectric breakdown is effected, thereby enabling the detection of dielectric breakdown during the discharge of the charge voltage to the body of a patient, as well as during charging of the high voltage capacitor.

When detection of dielectric breakdown occurs, operations similar to those described above are performed, that is, a switch 21a inhibits the delivery of high voltage while a notifying means 28 notifies the operator of dielectric breakdown.

Figure 5:
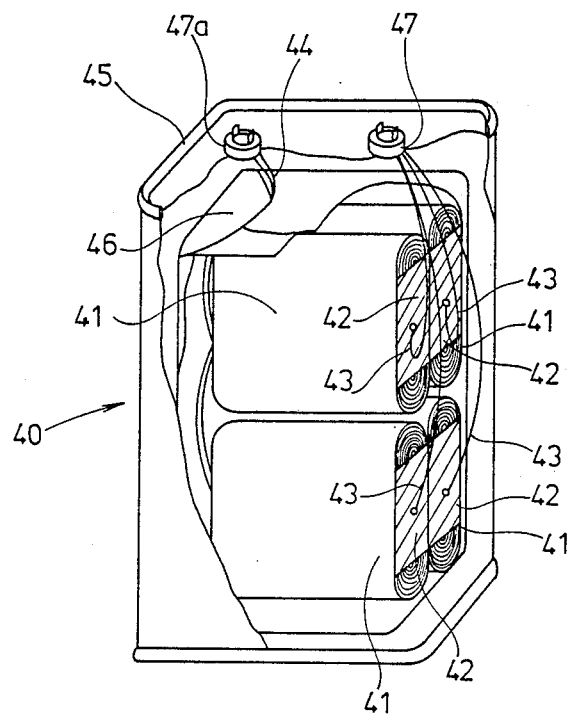
FIG. 5 is a partially broken-away perspective view of a high voltage capacitor for a defibrillation system constructed in accordance with a further embodiment of the present invention.

Referring to FIG. 5, there is shown a winding structure of a high voltage capacitor 40 constructed in accordance with the present invention. The capacitor is similar to the above-described high voltage capacitor 11.

Figure 6:
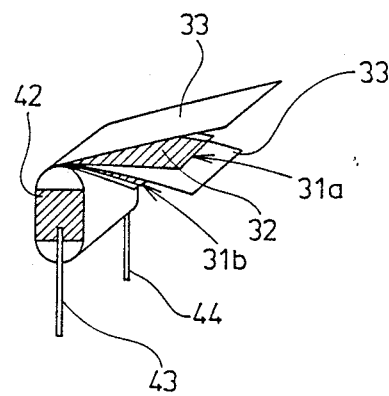
FIG. 6 is a perspective view of metallized plastic films of the capacitor constructed in accordance with the embodiment shown in FIG. 5.

In FIG. 5, the capacitor 40 includes, for instance, four (4) capacitor elements 41. As shown in FIG. 6, each capacitor element 41 is formed by winding up metallized plastic films 31a and 31b on which layers of a metal, e.g. aluminum, are deposited with protective films 33 being inserted between the films, in such a manner as to provide non-deposited portions at both lateral ends of the capacitor element. Metallic contacts 42 are provided on the end surfaces of each capacitor element 41 on both sides thereof. Resistance wires 43 are soldered to the end surfaces of the elements 41 on one side, while a lead wire 44 is soldered to the end surfaces on the other side so as to contact capacitor elements 41 in parallel. All the four capacitor elements 41 are surrounded by a pressed board 46 and are sealed within a case filled with insulating oil. The resistance wires 43 are connected to one end 47 of a pair of terminals 47, 47a formed on the upper surface of the case 45, while the single lead wire 44, extending from the junctions of the parallel connections, is connected to the other terminal 47a.

Each of the capacitor elements 41 has the capacity of, for instance, 10 microFarads, a dielectric strength of 10 kilovolts, and an internal resistance between the metallic contacts 42 at the end surface, which is about several Ohms and is smaller than the resistance of the patient's body during the discharge, that is about 50 Ohms. Resistance of each resistance wire 43 is set at substantially the same value as that of the above-mentioned internal resistance of each of the capacitor elements 41.

Figure 7:
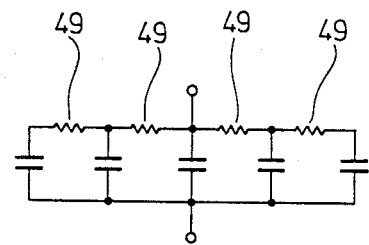
FIG. 7 is a schematic illustration showing the arrangement of a high-voltage capacitor constructed in accordance with a still further embodiment of the present invention.

In the foregoing embodiments, the number of the capacitor elements can be set at any value in accordance with any capacity, the ease of manufacturing, the allowable levels of dielectric breakdown noise, etc. The additional resistors may alternatively be interposed between the metallic contacts provided on the end surfaces on both sides of the capacitor elements. With this arrangement in which the metallic contacts are contacted in sequence by way of additional resistors 49, it is possible to make the number of additional resistors smaller by one than the number of elements, as shown in FIG. 7. The resistance of each interposed resistor is required to be at least equal to the internal resistance of each capacitor element, from the viewpoint of reducing the level of noise associated with dielectric breakdown. That resistance may be set to a larger value if it does not cause problems concerning energy loss and the time constant during the discharge via the paddle. The present invention may be used with metallized plastic films of another type, such as one-surface deposit type.

While the particular embodiments shown and described above have been proven to be useful in many applications involving the biomedical arts, further modifications herein disclosed will occur to persons skilled in the art to which the present invention pertains and all such modifications are deemed to be within the scope and spirit of the present invention defined by the appended claims.

What is claimed is:

1. A defibrillation system comprising:
    a high voltage generating circuit;
    a high voltage capacitor circuit which is adapted to be charged with a high voltage by said high voltage generating circuit and which includes a metallized plastic film capacitor;
    an output circuit which includes at least a switch and is adapted to apply said high voltage to a paddle mounted on the body of a patient;
    a charge abnormally detection circuit for detecting either a sharp increase in charge current or a sharp drop in charge voltage across said metallized plastic film capacitor which is caused by a dielectric breakdown thereof;
    a notifying means for notifying an operator of said defibrillation system of detected charge current or charge voltage abnormality, said notifying means responding to a detection signal produced by said charge abnormality detection circuit; and a switch circuit for inhibiting in response to said detection signal, the charging of said capacitor to a high voltage using said high voltage generating circuit.

2. The defibrillation system according to claim 1, wherein said charge abnormality detection circuit comprises:

a voltage divider for dividing the voltage across said high voltage capacitor circuit into a fraction of said voltage;

a peak holding circuit to which said fraction of said voltage across said high voltage capacitor circuit, is provided as an input and is maintained as a holding voltage; and a comparator for comparing said fraction voltage with a predetermined voltage lower than said holding voltage of said peak holding circuit and for generating a signal when said fraction voltage is below said predetermined voltage.

3. The defibrillation system according to claim 1, wherein said high voltage capacitor circuit is characterized by a normal charging and discharging characteristic, and said charge abnormality detection circuit comprises an analogue-to-digital convertor for digitizing a fraction of the voltage across said high voltage capacitor circuit, a memory for storing representing said normal charging and discharging characteristic of said high voltage capacitor circuit, and a central processing unit for comparing the digitized fraction voltage with the stored charging and discharging data as time passes.

4. A defibrillation system comprising:

a high voltage generating circuit;

a high voltage capacitor circuit which is adapted to be charged with a high voltage by said high voltage generating circuit and which includes a metallized plastic film capacitor;

an output circuit which includes at least a switch and is adapted to apply said high voltage to a paddle mounted on the body of a patient;

a charge abnormality detection circuit for detecting either a sharp increase in charge current or a sharp drop in charge voltage across said metallized plastic film capacitor which is caused by a dielectric breakdown thereof;

a notifying means for notifying an operator of said defibrillation system of detected charge current or charge voltage abnormality, said notifying means responding to a detection signal produced by said charge abnormality detection circuit; and a switch circuit for inhibiting in response to said detection signal, the charging of said capacitor to a high voltage using said high voltage generating circuit, wherein said metallized plastic film capacitor comprises a case, a plurality of capacitor elements, each having metallized plastic films wound-up to form said capacitor element having an end surface on each side thereof, and metallic contact portions being provided on said end surfaces of both sides of each said capacitor element and said plurality of capacitor elements being received in said case, a pair of capacitor terminals which extend from said case and which are connected to said metallic contact portions of said capacitor elements, and a plurality of resistors, each having a resistance at least equal to the internal resistance of each of said capacitor elements, and on at least one side of said capacitor elements, said resistors are connected to the metallic contact portions provided on said end surfaces of said capacitor elements.

5. A defibrillation system according to claim 4, wherein on one side of said capacitor element each said resistor is connected between one of said pair of capacitor terminals and the metallic contact portion provided on the end surfaces of said capacitor elements.

6. The defibrillation system according to claim 4, wherein said, on one side of said capacitor elements, each said resistor is connected between adjacent metallic portions provided on said end surfaces of said capacitor elements.

* * * * *

UNITED STATES PATENT AND TRADEMARK OFFICE
CERTIFICATE OF CORRECTION

PATENT NO. : 4,926,862

DATED : May 22, 1990

INVENTOR(S) : Miyajima et al.

Page 1 of 2

It is certified that error appears in the above-identified patent and that said Letters Patent is hereby corrected as shown below:

In the "ABSTRACT", Line 11, after "generating", change "cirucit" to --circuit--.

Column 1, line 17 - before "type", change "metalfilm" to --metal-film--.

Column 2, line 37 - before "film", change "metallized-plastic" to --metallized plastic--.

Column 4, line 68 - after "of the", change "peakholding" to --peak-holding--.

UNITED STATES PATENT AND TRADEMARK OFFICE
CERTIFICATE OF CORRECTION

PATENT NO. : 4,926,862

DATED : May 22, 1990

INVENTOR(S) : Miyajima et al.

It is certified that error appears in the above-identified patent and that said Letters Patent is hereby corrected as shown below:

Column 7, line 34 - before "said", change "a memory for storing representing" to --a memory for storing data representing--.

Column 8, line 42 - before "on", change "wherein said," to --wherein,--

Signed and Sealed this

Twelfth Day of May, 1992

Attest:

DOUGLAS B. COMER

Attesting Officer     Acting Commissioner of Patents and Trademarks